(12) United States Patent
Aldahlawi et al.

(10) Patent No.: US 12,125,206 B2
(45) Date of Patent: Oct. 22, 2024

(54) IN VIVO MAGNETIC RESONANCE IMAGE DISTORTION CHECK APPARATUS AND METHOD

(71) Applicant: Health Research, Inc., Buffalo, NY (US)

(72) Inventors: Ismail Aldahlawi, Buffalo, NY (US); Matthew Podgorsak, Williamsville, NY (US); Dheerendra Prasad, East Amherst, NY (US)

(73) Assignee: Health Research, Inc., Buffalo, NY (US)

( * ) Notice: Subject to any disclaimer, the term of this patent is extended or adjusted under 35 U.S.C. 154(b) by 425 days.

(21) Appl. No.: 17/430,790

(22) PCT Filed: Feb. 14, 2020

(86) PCT No.: PCT/US2020/018281
§ 371 (c)(1),
(2) Date: Aug. 13, 2021

(87) PCT Pub. No.: WO2020/168185
PCT Pub. Date: Aug. 20, 2020

(65) Prior Publication Data
US 2022/0130044 A1     Apr. 28, 2022

Related U.S. Application Data

(60) Provisional application No. 62/806,124, filed on Feb. 15, 2019.

(51) Int. Cl.
*G06T 7/00*      (2017.01)
*A61N 5/10*      (2006.01)
*G06T 7/60*      (2017.01)

(52) U.S. Cl.
CPC ............ *G06T 7/0014* (2013.01); *G06T 7/60* (2013.01); *A61N 5/103* (2013.01);
(Continued)

(58) Field of Classification Search
None
See application file for complete search history.

(56) References Cited

U.S. PATENT DOCUMENTS 10,297,022 B2 *   5/2019   Frank ................... G06T 11/008
2005/0049486 A1 *  3/2005   Urquhart ............... A61B 34/20
                                                          600/429
(Continued)

FOREIGN PATENT DOCUMENTS

EP           2160994 A   *   3/2010
JP       2006-136434 A        6/2006
(Continued)

OTHER PUBLICATIONS

PCT Internatnational Search Report and Written Opinion for corresponding Application No. PCT/US2020/018281, date of mailing May 11, 2020, [48 pages].

*Primary Examiner* — Mohammed Rachedine
(74) *Attorney, Agent, or Firm* — Harris Beach PLLC; Laura W. Smalley

(57) ABSTRACT

An apparatus for identifying and quantifying image distortions within a patient magnetic resonance image set comprises a structure of magnetic resonance compatible materials with a high level of rigidity, where the structure is configured to cover the whole image volume of the brain region of the patient and sized to fit within a brain magnetic resonance coil when worn by a patient. A plurality of magnetic resonance fiducial markers is placed on the structure, thereby permitting the measurement of three-dimensional distances between the markers when the patient undergoes a magnetic resonance imaging procedure. Also (Continued)

presented is a process for identifying and quantifying image distortions within a patient magnetic resonance image set using the apparatus where the geometrical distortion is quantified and compared with a set threshold or a standard image.

12 Claims, 2 Drawing Sheets

(52) U.S. Cl.
CPC .................. *G06T 2200/04* (2013.01); *G06T 2207/10028* (2013.01); *G06T 2207/10088* (2013.01); *G06T 2207/30016* (2013.01)

(56) References Cited

U.S. PATENT DOCUMENTS

| | | |
|---|---|---|
| 2007/0018645 A1 | 1/2007 | Wang et al. |
| 2012/0184844 A1 | 7/2012 | Gielen et al. |
| 2014/0266198 A1 | 9/2014 | Tadic et al. |
| 2016/0217555 A1* | 7/2016 | Ertel .................. G01R 33/5608 |
| 2018/0136295 A1* | 5/2018 | Tadic .................... G01R 33/58 |

FOREIGN PATENT DOCUMENTS

| | | | | |
|---|---|---|---|---|
| WO | WO-2015171056 A1 * | 11/2015 | ............. | A61B 5/055 |
| WO | WO-2018171880 A1 * | 9/2018 | ........... | G06T 7/0016 |

* cited by examiner

IN VIVO MAGNETIC RESONANCE IMAGE DISTORTION CHECK APPARATUS AND METHOD

CROSS-REFERENCE TO RELATED APPLICATIONS

This application is a national stage (371) application of International Application No. PCT/US2020/018281, filed Feb. 14, 2020, which claims priority to and the benefit of U.S. provisional patent application Ser. No. 62/806,124, entitled In Vivo Magnetic Resonance Image Distortion Check Apparatus and Method, filed Feb. 15, 2019. These applications are incorporated herein by reference in their entirety.

I. FIELD OF THE INVENTION

The present invention is directed to an apparatus and methods for identifying and quantifying image distortions within a patient magnetic resonance imaging (MRI) image set.

II. SUMMARY OF THE INVENTION

An embodiment of the claimed apparatus for identifying and quantifying image distortions within a patient magnetic resonance image set, comprises a structure of magnetic resonance compatible materials with a high level of rigidity, where the structure is configured to cover the whole image volume of the brain region of the patient and sized to fit within a brain magnetic resonance coil when worn by a patient; and a plurality of magnetic resonance fiducial markers on the structure are configured to cover the image volume of the brain of the patient, thereby permitting the measurement of three-dimensional distances between the markers when the patient undergoes a magnetic resonance imaging procedure. In certain aspects of the invention, the structure may be formed in the shape of an eyeglass frame, a helmet or frame.

Another aspect of the invention comprises a process for identifying and quantifying image distortions within a patient magnetic resonance image set, comprising the steps of: providing a structure of non-magnetic and magnetic resonance compatible materials with a high level of rigidity, where the structure is configured to cover the whole image volume of the brain region of the patient and sized to fit within a brain magnetic resonance coil; providing a plurality of magnetic resonance fiducial markers placed on the structure; placing the structure on the head of a patient; scanning the structure with the patient while the patient is undergoing a magnetic resonance imaging procedure using a prescribed clinical scanning protocol; exporting an image set resulting from the scanning using Digital Imaging and Communications in Medicine (DICOM) standards to a viewing/analyzing software; measuring marker distances and analyzing geometrical distortion on the image set using the viewing/analyzing software; quantifying and comparing the geometrical distortion with a set threshold or a standard image; and if the geometrical distortion meets the threshold or standard, using the image set for stereotactic radiosurgery treatment planning; or if the distortion set does not meet the threshold or standard, generating a second image set under changed imaging conditions, including removing distortion causes, using a different scanning protocol, or scanning with a different imaging modality. Analyzing the geometrical distortion may be performed by various methods, such as checking three-dimensional distances between markers shown in the image set and comparing the distances with reference distances obtained from the physical design of the structure; checking the three-dimensional distances between markers shown in the image set and comparing them with distances derived from non-distorted images; or comparing the image of the structure with a reference image. The method may be performed with various embodiments of the apparatus such as where, for example, the structure is formed in the shape of an eyeglass frame, a helmet or frame.

III. BRIEF DESCRIPTION OF THE DRAWINGS

IV. DETAILED DESCRIPTION OF THE INVENTION

Figure 1:
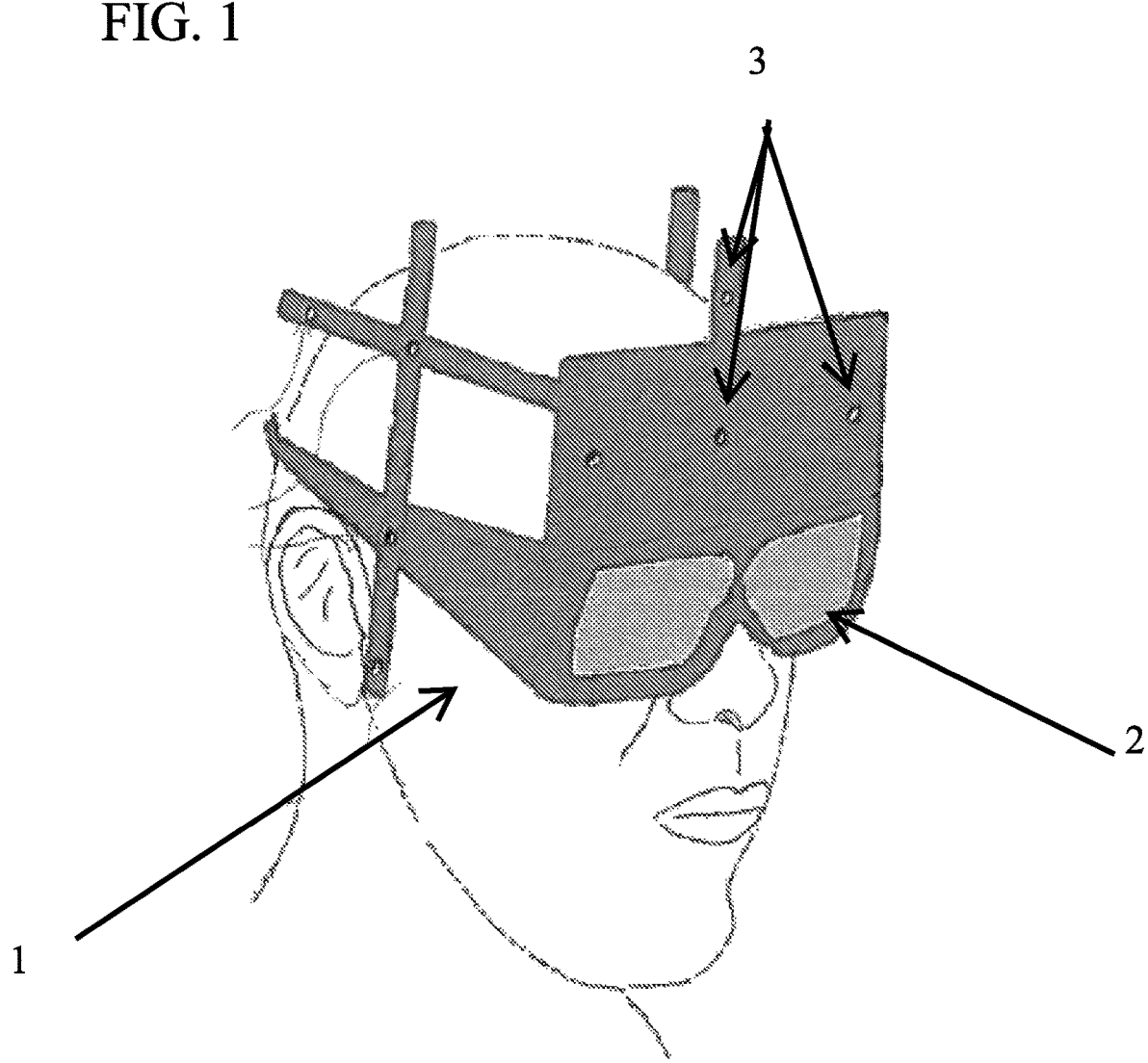
FIG. 1 shows a perspective view of one embodiment of the invention in the form of a rigid eyeglasses frame adapted to be worn by a patient undergoing magnetic resonance imaging.

The spatial accuracy in planning magnetic resonance (MR) images is a critical component of safe and accurate patient treatment using stereotactic radiosurgery of intracranial lesions. MR images can have considerable geometrical distortion due to the difference in scanning pulse sequences, difference in magnetic susceptibilities of individual patients, and the presence of magnetic-susceptible objects such as metallic surgical clips or staples, and stereotactic headframes. Traditional skull immobilization for stereotactic radiosurgery frame treatments uses a stereotactic headframe invasively attached to a patient's skull. An MR indicator device can be attached to the headframe. This MR indicator device, primarily used for stereotactic space coordinate definition, has an underlying advantage of enabling verification of the extent of distortion within MR images at the time of stereotactic space definition.

With "frameless" stereotactic radiosurgery treatments, however, an MR indicator device is not used. Instead, stereotactic space coordinates are defined using an integrated imaging modality on the treatment unit (e.g., a cone-beam CT on the Gamma Knife unit). When an integrated imaging modality is used, geometrical distortions in the planning MR images may be missed, leading to compromised positional accuracy in target delineation and radiation shot placement when performing frameless stereotactic radiosurgery treatments. A solution to this problem is to have a geometrical distortion check apparatus scanned with the patient during planning MR imaging where the device has a known fiducial marker geometry.

The current available MR indicator device used primarily for stereotactic space coordinate definition with frame immobilization in stereotactic radiosurgery has two main limitations: 1) it can only be attached to an immobilizing frame, and 2) it can be too large to fit inside a multichannel brain MR coil. The disclosed apparatus is designed to overcome these limitations as it can be imaged unattached to other devices with the patient head in a confined brain MR coil used for imaging. Commercial MR-image distortion check tools exist. However, these tools are meant for a stand-alone application as a general check for image distortion, and thus they are too bulky to be included with patient scanning. The disclosed apparatus is designed to be scanned with the patient to check not only the scanner-specific image distortion, but also image distortion introduced by the presence of magnetic objects in the patient and the difference in magnetic susceptibilities of individual patients.

Disclosed is a geometrical distortion check apparatus that can be scanned with the patient during MR imaging. The apparatus can be used to identify and quantify image distortions within a patient magnetic resonance imaging (MRI) image set. In one embodiment, several fiducial markers are placed on or embedded within a rigid holding apparatus (e.g., box or frame) made of non-magnetic materials covering the whole image volume of the brain region. The apparatus will be scanned with the patient undergoing an MR imaging procedure. A check for image distortion is performed by comparing the three-dimensional distances between the MR fiducial markers in the images with reference distances. One application for use of this apparatus is in frameless stereotactic radiosurgery that uses MR images for accurate target localization within the brain. It may be recognized that the disclosed apparatus and method may be used in other applications where identifying and quantifying image distortions within a patient magnetic resonance imaging (MRI) image set are desirable, such as radiotherapy and calculating predicted radiation dosages.

One embodiment of the disclosed apparatus is 1) made of a material of a high level of rigidity; 2) made of non-magnetic and MR compatible materials; 3) precisely machined with high spatial accuracy; 4) embedded or attached with MR-visible markers that are highly localized; and 5) confined enough to fit inside a brain MR coil with enough room for the patient head. an apparatus meeting the specification above could be made such that it is wearable by the patient during the MR imaging scanning (e.g., an eyeglasses frame or a helmet). FIG. 1 shows an example of such a wearable eyeglasses frame device. It will be recognized by one of ordinary skill in the art that the apparatus can take other forms such as a frame or box, or other shapes that cover the whole image volume of the brain region and that can be scanned with the patient undergoing an MR imaging procedure.

The apparatus is made of non-magnetic and MR compatible materials, such as, for example, titanium, certain titanium alloys, Co—Cr alloys, tantalum, and implant grade stainless steels, other such materials known in the art, or combinations thereof. Certain polymer (plastic) and ceramic materials may also be suitable. The material should be sufficiently rigid so that it does not bend or deform when worn by the patient before, during and after the procedure. Commercially available fiducial markers for placement on the apparatus are available in a range of sizes and shapes.

One embodiment of the invention has the form of a rigid eyeglasses frame adapted to be worn by a patient undergoing magnetic resonance imaging is shown in FIG. 1. The frame 1 fits on the head of the patient. The frame 1 optionally has lenses or lens shaped areas 3 therein. A plurality of magnetic resonance (MR)-visible fiducial markers 4 are located on the frame 1 in a manner to allow the three-dimensional distances between the fiducial markers 4 to be compared with reference distances.

Figure 2:
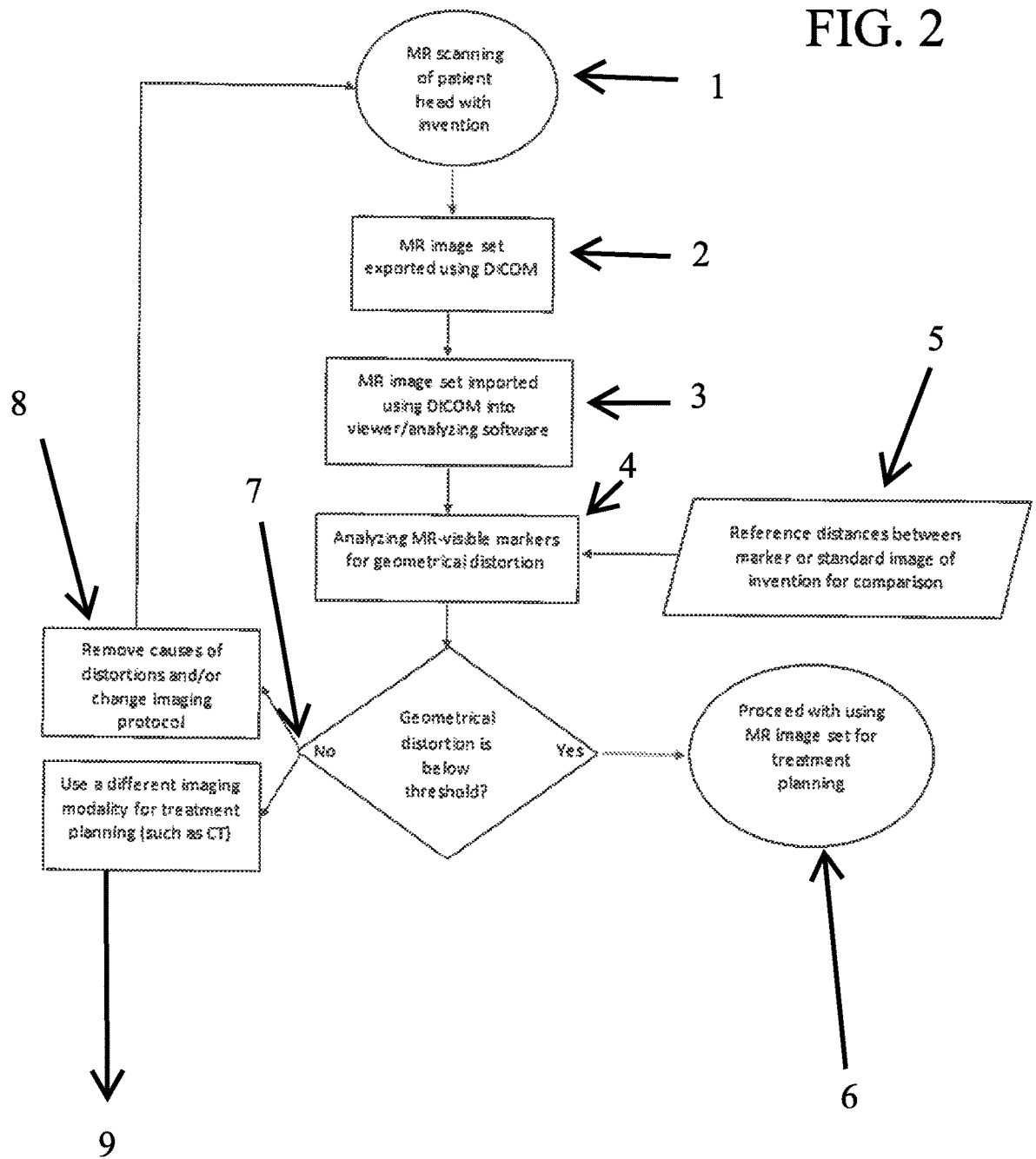
FIG. 2 illustrates a process for using an embodiment of the invention.

The process for using such an apparatus is as shown in FIG. 2. First, the apparatus is scanned with the patient using the prescribed clinical scanning protocol (1). The resulting MR image set is then exported using the Digital Imaging and Communications in Medicine (DICOM) standards to a viewing/analyzing software (2). The MR image set is then imported using the DICOM standards to the viewing/analyzing software (3). The viewing/analyzing software is then used for measuring marker distances and analyzing geometrical distortion on the MR image set (4).

The geometrical distortion is quantified and compared with a set threshold or a standard image (5). If the geometrical distortion is acceptable (i.e., meeting the threshold/standard), then the MR image set can be sent to be used for stereotactic radiosurgery treatment planning (6). If the distortion is not acceptable, then this MR image set shall not be used for treatment planning and a different image set is to be taken and assessed for suitability for treatment planning (7) (e.g., repeated MR images after removing distortion causes, MR scanning with a different scanning protocol (8), or scanning with a different imaging modality such as computed-tomography) (9). The analysis of the geometrical distortion can be done by (10) checking the three-dimensional distances between markers and comparing them with reference distances obtained from the physical design or using other non-distorted images (e.g., using a CT scan). An alternative method is to compare the extracted MR image of the device with a reference image to check for distortion (e.g., by image co-registration with a CT scan or a reference non-distorted MR scan of the device). A software code could be used for automatic determination of markers and analysis of distortion. The foregoing methods of analyzing geometrical distortion represent embodiments of the method but other methods of analysis known to one skilled in the art may be used.

While the disclosed invention has been described as having a preferred design, it is understood that it is capable of further modifications, and uses and adaptations of the invention following in general the principle of the invention and including such departures from the present disclosure as come within the known or customary practice in the art to which the invention pertains, and as may be applied to the central features described above and falling within the scope of the invention or limits of the claims.

What is claimed is:

1. A process for identifying and quantifying image distortions within a patient magnetic resonance image set, comprising the steps of:
   providing a structure of magnetic resonance compatible materials with a high level of rigidity, the structure configured to cover the whole image volume of the brain region of the patient and sized to fit within a brain magnetic resonance coil;
   providing a plurality of magnetic resonance fiducial markers placed on the structure;
   placing the structure on the head of a patient;
   scanning the structure with the patient while the patient is undergoing a magnetic resonance imaging procedure using a prescribed clinical scanning protocol;
   exporting an image set resulting from the scanning using Digital Imaging and Communications in Medicine (DICOM) standards to a viewing/analyzing software;
   measuring marker distances and analyzing geometrical distortion on the image set using the viewing/analyzing software;
   quantifying and comparing the geometrical distortion with a set threshold or a standard image; and
   if the geometrical distortion meets the threshold or standard, using the image set for stereotactic radiosurgery treatment planning; or
   if the distortion set does not meet the threshold or standard, generating a second image set under changed imaging conditions, including removing distortion causes, using a different scanning protocol, or scanning with a different imaging modality.

2. The method of claim 1, wherein analyzing the geometrical distortion comprises checking three-dimensional distances between markers shown in the image set and comparing the distances with reference distances obtained from the physical design of the structure.

3. The method of claim 1, wherein analyzing the geometrical distortion comprises checking the three-dimensional distances between markers shown in the image set and comparing them with distances derived from non-distorted images.

4. The method of claim 1, wherein analyzing the geometrical distortion comprises comparing the image of the structure with a reference image.

5. The method of claim 1, wherein the structure is formed in the shape of an eyeglass frame.

6. The method of claim 5, wherein analyzing the geometrical distortion comprises checking three-dimensional distances between markers shown in the image set and comparing the distances with reference distances obtained from the physical design of the structure.

7. The method of claim 5, wherein analyzing the geometrical distortion comprises checking three-dimensional distances between markers shown in the image set and comparing the distances with distances derived from non-distorted images.

8. The method of claim 5, wherein analyzing the geometrical distortion comprises comparing the image of the structure with a reference image.

9. The method of claim 1, wherein the structure is formed in the shape of a frame.

10. The method of claim 9, wherein analyzing the geometrical distortion comprises checking three-dimensional distances between markers shown in the image set and comparing the distances with reference distances obtained from the physical design of the structure.

11. The method of claim 9, wherein analyzing the geometrical distortion comprises checking three-dimensional distances between markers shown in the image set and comparing the distances with distances derived from non-distorted images.

12. The method of claim 9, wherein analyzing the geometrical distortion comprises comparing the image of the structure with a reference image.

* * * * *